(12) United States Patent
Styrc

(10) Patent No.: US 8,512,396 B2
(45) Date of Patent: Aug. 20, 2013

(54) DEVICE FOR TREATING A BLOOD CIRCULATION CONDUIT

(75) Inventor: Witold Styrc, Kopstal (LU)

(73) Assignee: Laboratoires Perouse, Ivry le Temple (FR)

( * ) Notice: Subject to any disclaimer, the term of this patent is extended or adjusted under 35 U.S.C. 154(b) by 420 days.

(21) Appl. No.: 12/677,314

(22) PCT Filed: Sep. 11, 2008

(86) PCT No.: PCT/FR2008/051621
§ 371 (c)(1),
(2), (4) Date: Jun. 24, 2010

(87) PCT Pub. No.: WO2009/044082
PCT Pub. Date: Apr. 9, 2009

(65) Prior Publication Data
US 2010/0280589 A1 Nov. 4, 2010

(30) Foreign Application Priority Data

Sep. 11, 2007 (FR) ...................................... 07 57493
Jun. 11, 2008 (FR) ...................................... 08 53879

(51) Int. Cl.
*A61F 2/84* (2006.01)
(52) U.S. Cl.
USPC .......................... 623/1.24; 623/1.26; 623/2.18
(58) Field of Classification Search
None
See application file for complete search history.

(56) References Cited

U.S. PATENT DOCUMENTS

| | | |
|---|---|---|
| 2005/0090834 A1* | 4/2005 | Chiang et al. ................. 606/108 |
| 2005/0137688 A1 | 6/2005 | Salahieh et al. |
| 2005/0283231 A1 | 12/2005 | Haug et al. |
| 2006/0058872 A1 | 3/2006 | Salahieh et al. |
| 2006/0149360 A1 | 7/2006 | Schwammenthal et al. |

OTHER PUBLICATIONS

International Search Report, dated May 8, 2009, from corresponding PCT application.

* cited by examiner

*Primary Examiner* — Thomas J Sweet
*Assistant Examiner* — Megan Wolf
(74) *Attorney, Agent, or Firm* — Young & Thompson

(57) ABSTRACT

This device (10) includes an implant (20) which has a tubular endoprosthesis (30) with a radially deployable framework (36). The implant (20) includes a flexible interposition member (24) mounted movably on the endoprosthesis (30) so as to be interposed between the outer surface (40) and a blood circulation conduit (14). The device (10) includes a deployment tool (26) which can adopt a configuration for insertion of the implant (20) and a configuration for release of the implant (20). In the configuration for insertion of the implant (20), the flexible member (24) includes at least one free part (68) held axially away from the outer surface (40) in order to minimize the radial dimension of the implant (20). The free part (68) is at least partly displaceable against the outer surface (40) when the tool (26) moves from its configuration for insertion to its configuration for release.

13 Claims, 14 Drawing Sheets

DEVICE FOR TREATING A BLOOD CIRCULATION CONDUIT

The present invention relates to a device for treating a blood circulation conduit, of the type comprising:
- an implant for placing in the conduit, the implant comprising:
- a tubular endoprosthesis with an axis having a framework which is radially deployable between a contracted state and a dilated state, the framework having an outer surface delimited axially by an axial edge;
- at least one interposition member which is more flexible than the framework, the flexible interposition member being mounted movably on the endoprosthesis for interposition between the outer surface and the conduit; and
- a tool for deploying the implant, which tool can adopt a configuration for insertion of the implant in the conduit, in which the tool holds the framework in its contracted state, and a configuration for release of the implant, in which the framework adopts its dilated state.

The device applies in particular to the treatment of defective native valves, such as cardiac valves or pulmonary valves.

The heart has valves at the outlet of the right ventricle (pulmonary valve) and of the left ventricle (aortic valve).

These valves ensure that the blood flows in one direction, preventing reflux at the end of ventricular contraction.

However, disease or malformation affect the correct functioning of the valves.

In particular, valves are subject to calcification which allows reflux or regurgitation towards the ventricle that has expelled the blood. The regurgitation problem leads to abnormal dilation of the ventricle which eventually causes heart failure.

To treat this type of disease surgically, implanting an endovalve between the laminas of the diseased native valve is known. The endovalve comprises a tubular endoprosthesis formed by a self-expandable mesh and a flexible obturator or valve which is usually made of animal tissue. The flexible obturator is fixed permanently in the endoprosthesis.

This type of endovalve can be implanted endoluminally, which considerably reduces the risks associated with implanting the valve, particularly in terms of mortality.

In some cases, endovalves do not give complete satisfaction after implantation. In fact, although the outer surface of the endoprosthesis is applied spontaneously against the seat of the native valve by laying the laminas flat between the seat and the outer surface of the endoprosthesis, leakages may still remain around the outer surface of the endoprosthesis, particularly at the commissures between the laminas of the native valve. These leakages occur in over 50% of patients who have undergone such an operation.

To overcome this problem, arranging interposition members with a substantial radial thickness is known, in particular from US 2005/0137688. These interposition members are for example fixed directly on the outer surface of the endoprosthesis or are formed from an outer skirt turned down against the outer surface of the endoprosthesis. Such interposition members are deformable. They therefore fill the gaps that may occur around the valve.

However, interposition members placed around the endoprosthesis increase the radial dimension of the endovalve. The deployment tools used to implant such endovalves therefore have a radial dimension which is not insignificant, which may interfere with their implantation in the body.

An object of the invention is therefore to obtain a treatment device comprising an implant that can be implanted in a sealed manner in a blood circulation conduit of irregular section, while having a small radial dimension when it is inserted in the patient's body.

The invention therefore relates to a device of the above-mentioned type, characterised in that in the configuration for insertion, the flexible interposition member comprises at least one free part held axially away from the outer surface beyond the axial edge to minimise the radial dimension of the implant, the free part being at least partly displaceable against the outer surface when the tool moves from its configuration for insertion to its configuration for release.

SUMMARY OF THE INVENTION

The device according to the invention may comprise one or more of the following characteristics, taken in isolation or in any technically possible combination(s):
- the interposition member comprises at least a flexible peripheral skirt having an edge fixed to the endoprosthesis and a free edge, the skirt being displaceable between a configuration of reduced radial dimension in which the free edge is placed axially away from the axial edge of the outer surface, which the skirt adopts in the configuration for insertion, and a configuration turned down against the outer surface which the skirt adopts in the configuration for release;
- the interposition member comprises at least one radial sealing cushion which projects radially relative to the skirt;
- the or each tie releasably connect the free part and the deployment tool, the or each actuation tie being axially displaceable relative to the endoprosthesis to pull the free part towards the outer surface when the deployment tool moves from its configuration for insertion to its configuration for release;
- the or each actuation tie can be broken by axial traction;
- the or each actuation tie comprises a locking loop, the deployment tool comprising a pin which is movable between an engaged position in the locking loop, in which the axial displacement of the actuation tie relative to the endoprosthesis causes the axial displacement of the free part relative to the endoprosthesis, and a released position outside the locking loop, in which the axial displacement of the tie causes its release relative to the free part;
- the deployment tool comprises a sheath for housing the implant, which can be displaced axially relative to the implant, the actuation tie being engaged releasably in the sheath, and the displacement of the sheath away from the endoprosthesis causing the displacement of the free part towards the outer surface by traction on the tie;
- the deployment tool comprises a stent for holding the endoprosthesis axially before the radial deployment of the framework, the actuation tie being engaged in the stent and being movable relative to the endoprosthesis through the stent in order to be actuated from a proximal end of the stent;
- the flexible interposition member is spontaneously deformable when the deployment tool moves from its configuration for insertion to its configuration for release, in order to spontaneously cause the free part to be at least partly displaced against the outer surface;
- the flexible interposition member comprises at least one resilient component connecting the free part to the outer surface, the resilient component being held in an unstable position under tension by the deployment tool in the configuration for insertion;

the framework has an inner surface delimiting a central blood circulation passage, the implant comprising a valve fixed to the inner surface to selectively close the central passage; and it comprises at least one tie for actuating the interposition member, the actuation tie having at least a first point of connection to the interposition member and at least second and third points of connection to the framework, the second and third connection points being spaced angularly on the framework about the axis;

the movement of the framework of the endoprosthesis between its contracted state and its dilated state causing the distance separating the second connection point and the third connection point to increase, and the axial displacement of the first connection point between a position axially remote from the second and third connection points and a position axially closer to the second and third connection points, in which the first connection point is situated facing the outer surface.

BRIEF DESCRIPTION OF THE DRAWINGS

The invention will be better understood on reading the description that follows, given solely by way of example and with reference to the accompanying drawings, in which.

DETAILED DESCRIPTION OF THE PREFERRED EMBODIMENTS

Figure 1:
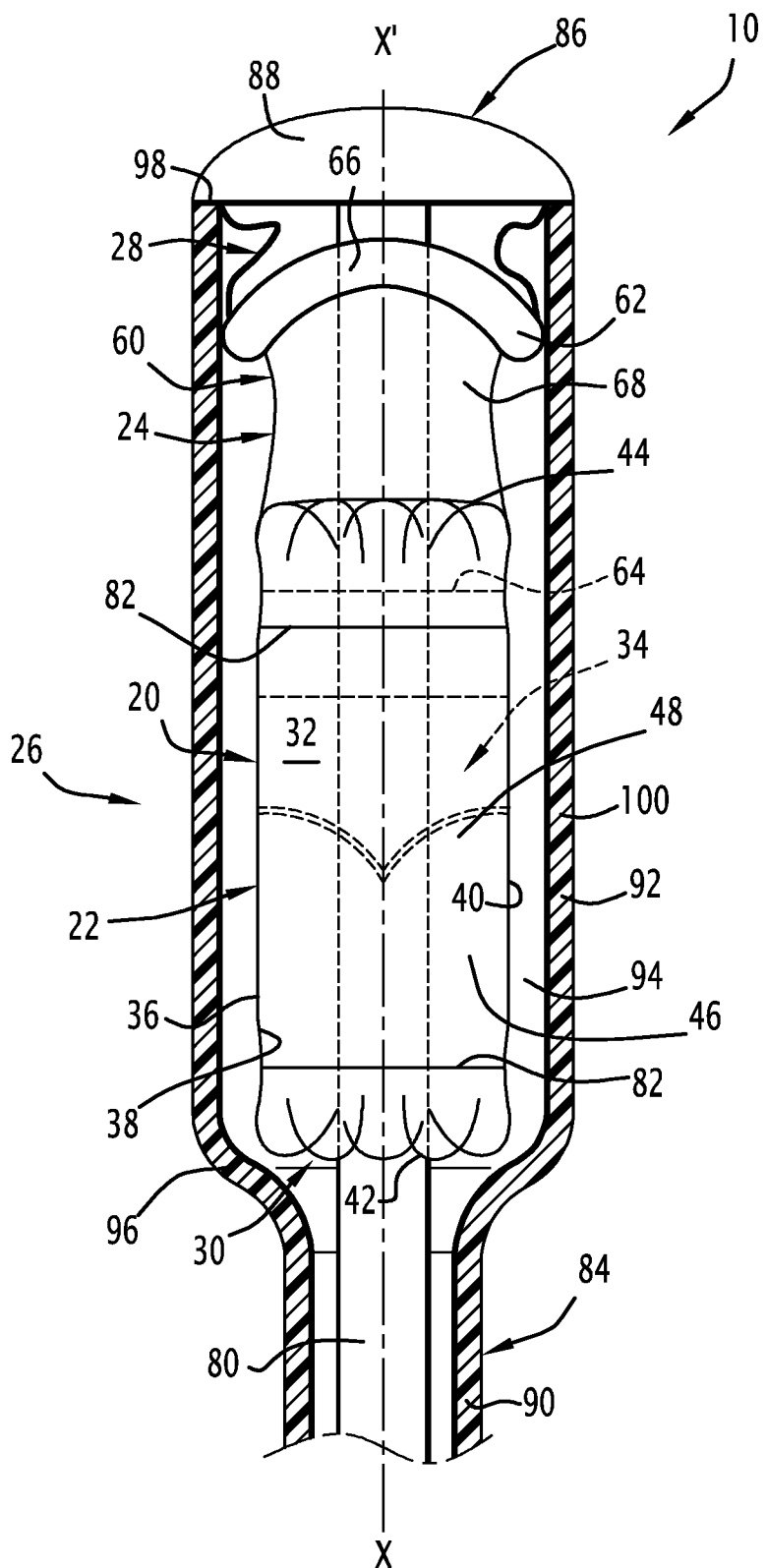
FIG. 1 is a diagrammatic view in part cross-section of a first treatment device according to the invention, with the deployment tool adopting a configuration for insertion of the implant in the body.

In the rest of this document, the terms "distal" and "proximal" are understood as regards the treatment device with reference to a user of the device situated outside the patient's body.

FIGS. 1 to 4 show a first treatment device 10 according to the invention. The device is designed in particular for implanting an endovalve comprising a tubular endoprosthesis and a valve as a replacement for a native cardiac valve 12, which can be seen in FIGS. 2 and 4.

As shown in these figures, the native valve 12 is situated in a blood circulation conduit 14 delimited internally by a peripheral wall 16. The native valve 12 comprises a plurality of laminas 18 which can be moved in the conduit 14 from the wall 16.

As shown in FIGS. 1 to 4, the device 10 comprises an implant 20 which comprises an endovalve 22 and an interposition member 24, mounted permanently on the endovalve 22 to provide a seal around the endovalve 22 between the endovalve 22 and the circulation conduit 14. The device 10 also comprises a tool 26 for deploying the endovalve, and means 28 for displacing the interposition member 24 in order to turn it down around the endovalve 22 when the implant 20 is deployed.

Figure 4:
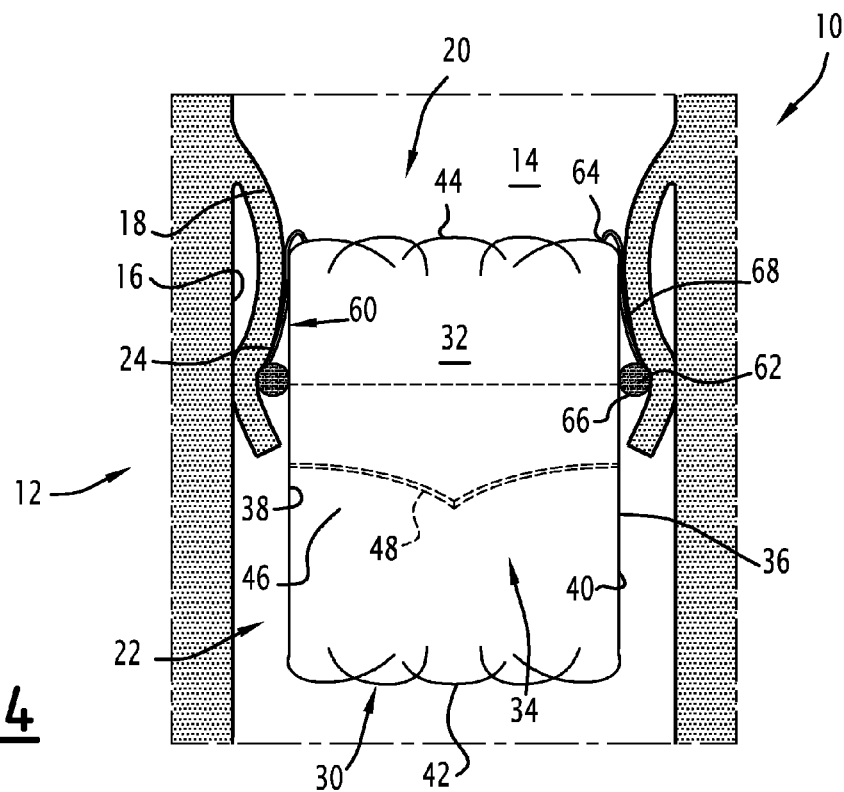
FIG. 4 is a view of the implant after deployment in the blood circulation conduit.

As shown in FIGS. 1 and 4, the endovalve 22 comprises a tubular endoprosthesis 30 delimiting a central blood circulation passage 32, and a valve 34 or obturator attached to the endoprosthesis 30 inside the passage 32.

The endoprosthesis 30 consists of an openwork tubular framework 36 comprising a mesh of threads which have spring-like properties. The framework 36 is obtained by weaving at least one stainless steel thread made of a shape-memory alloy or a polymer. In a variant, the framework 36 is obtained by laser cutting a tube.

The framework 36 defines an inner peripheral surface 38 and an outer peripheral surface 40 having substantially an axis X-X'. The surfaces 38 and 40 are substantially cylindrical and extend about the axis X-X' between a proximal peripheral edge 42, situated near the bottom in FIG. 1 and a distal peripheral edge 44, situated near the top in FIG. 1.

The inner surface 38 defines internally the central passage 32. The outer surface 40 is to be applied at least in part against the wall 16 and/or against the laminas 18, as will be seen below.

The framework 36 of the endoprosthesis 30 can be deployed between a contracted state in which it has a small diameter in order to introduce it in the conduit 14, and a dilated state, which constitutes its rest state, in which it has a large diameter. In the example shown in FIGS. 1 to 4, the framework 36 can be deployed spontaneously between its contracted state and its dilated state.

The valve 34 is produced for example from a native valve of an animal such as a pig. In a variant, it is produced from natural tissues such as bovine or ovine pericardium, or from synthetic tissues.

Conventionally, the valve 34 comprises a tubular base 46 fixed to the inner surface 38 of the framework 36, and three flexible obturation laminas 48 of the central passage 32 which extend downwards to the base 38.

The laminas 48 are radially displaceable towards the axis X-X' of the passage 38 between an obturation position, in which they substantially completely prevent the blood from passing through the passage 32, and a release position of the passage 32 in which they are substantially laid flat against the inner surface 38 and allow the blood to pass through the passage 32.

In the obturation position, the laminas 48 have a convergent cross-section towards the proximal edge 42 of the valve.

In the example shown in FIGS. 1 to 4, the interposition member 24 comprises a flexible peripheral skirt 60 attached to the tubular endoprosthesis 30, and an annular sealing cushion 62 fixed to the skirt 60.

The skirt 60 is produced for example from a fabric such as Dacron or from a polymer film. It has a substantially continuous cylindrical or tapered form about the axis X-X'. In particular, the skirt 60 is more flexible than the framework 36 of the endoprosthesis 12.

The skirt 60 extends between a connection edge 64 to the endoprosthesis 30 fixed to the framework 36, and a free edge 66.

The connection edge 64 is arranged in the central passage 32 in the vicinity of the distal edge 44. It is fixed to the inner surface 38 of the framework by known means, such as adhesive bonding or stitching.

As will be seen below, the skirt 60 defines, between its connection edge 64 and its free edge 66, a free part 68 which may have a length of more than zero projecting axially outside the central passage 32 beyond the distal edge 44.

The skirt 60 has a length taken along the X-X' axis between its connection edge 64 and its free edge 66 which is 20% greater than the length of the endoprosthesis 30.

In the example shown in FIG. 1, the annular cushion 62 is attached to the outside of the skirt 60, along its free edge 66. The cushion 62 forms a deformable annular collar made of compressible foam for example.

According to the invention, the skirt 60 and the annular cushion 62 are displaceable together between a configuration of minimum radial dimension, placed in the axial extension of the endoprosthesis 30, illustrated in FIG. 1, and a configuration for interposition between the endoprosthesis 30 and the conduit 14, turned down against the outer surface 40 of the endoprosthesis 30.

In the configuration of minimum radial dimension, which can be seen in FIG. 1, the skirt 60 extends axially in the extension of the endoprosthesis 30 beyond the distal edge 44. In this example, the free edge 66 is arranged axially away from the distal edge 44 of the endoprosthesis at a maximum distance from the distal edge 44.

The free part 68 and the annular cushion 62 are thus held projecting axially in the extension of the outer surface 40, axially away from said surface. The length of the free part 68 projecting away from the outer surface 40 beyond the edge 44 is maximal.

Figure 14:
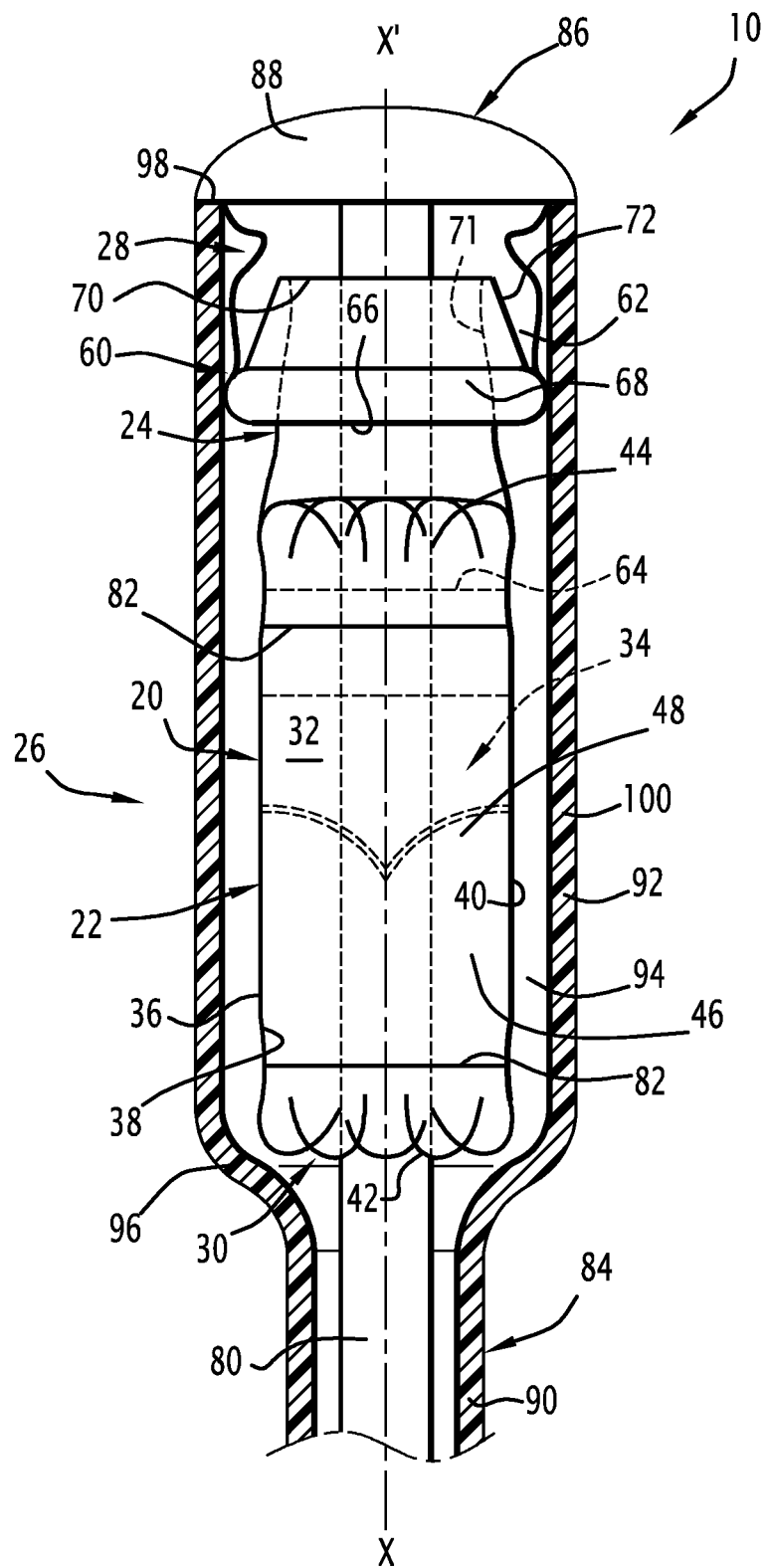
FIG. 14 is a view similar to FIG. 1 of a variant of the device of FIG. 1.

In a variant shown in FIG. 14, the skirt 60 has a free edge 66 partly turned down towards the connection edge 64 in its configuration of minimum radial dimension. The skirt 60 thus defines an annular fold 70 situated at the maximum distance from the edge 44. It therefore comprises an inner portion 71 situated between the connection edge 64 and the fold 70 and an outer portion 72 which extends around the inner portion between the fold 70 and the free edge 66 of the skirt 60.

In the configuration of minimum radial dimension, the outer portion 72 and the free edge 66 are situated axially away from the distal edge 44, away from the outer surface 40.

Figure 2:
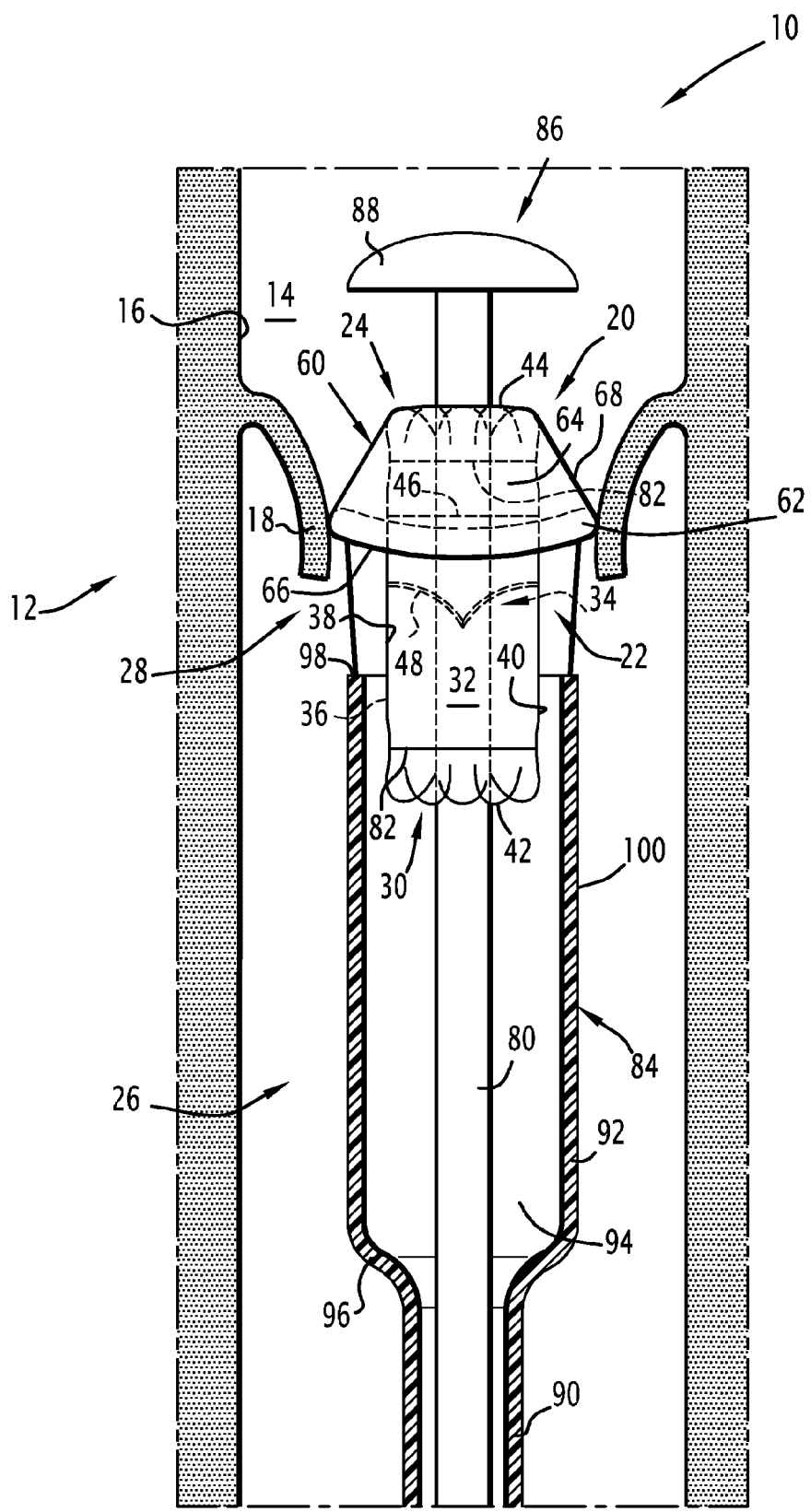
FIG. 2 is a view similar to FIG. 1, while the implant replacing a defective native valve is being put in place.

In the turned-down configuration, shown in FIG. 2, the skirt 60 has been turned down against the outer surface 40 of the endoprosthesis 30. In this configuration, the free edge 66 and the annular cushion 62 extend facing the outer surface 40, around this surface. In this example, the cushion 62 is also placed substantially level with the valve 34, as shown in FIG. 4.

The free part 68 covers externally the distal region of the endoprosthesis around the outer surface 40. The skirt 60 forms a peripheral fold around the distal edge 44 of the endoprosthesis.

In the example shown in FIG. 1, the deployment tool 26 comprises a stent 80 to support and axially maintain the endovalve 22 in the conduit 14, threadlike ties 82 for holding the framework 36 in its contracted state against the stent 80, and a protection sheath 84 suitable for receiving the implant 20 and the stent 80 internally.

The deployment tool 26 is of the type for example described in French application FR-A-2 863 160 by the applicant.

As described in the above-mentioned application, the stent 80 extends between a proximal end (not illustrated) for manipulation by a surgeon outside the human body, and a distal end 86 for insertion in the conduit 14 as far as the valve 12. At its distal end 86, the stent 80 is provided with a profiled tip 88 so that the deployment tool 26 containing the implant 20 can be inserted endoluminally in the conduit 14 without damage.

As will be seen below, the tool 26 can be manipulated to cause it to move from a configuration for insertion of the implant 20 in the conduit 14 to a configuration for release of the implant 20 in the conduit 14.

In the configuration for insertion, the implant 20 is mounted coaxially around the stent 80, beneath the tip 88 in the vicinity of the distal end 86. The stent 80 is therefore inserted in the central passage 32 and through the skirt 60.

As described in the above-mentioned application, the threadlike ties 82 are releasable. They encircle the framework 36 of the endoprosthesis 30 in the vicinity of its distal edge 44 and its proximal edge 42 respectively.

The ties 82 can be actuated and released from the proximal end of the stent 80 between a configuration for holding the framework 36 in its contracted state against the stent 80, and a configuration for release of the framework 36 in which the framework 36 adopts its dilated state.

The sheath 84 is mounted coaxially around the stent 80 and the implant 20.

It has a proximal stem 90 and a flared distal head 92 with a diameter greater than that of the stem 90 and defining internally a cylindrical housing 94 for receiving the implant 20.

The head 92 extends between a proximal shoulder 96 which it forms with the stem 90 and a distal circumferential edge 98 to be positioned resting against the tip 88.

The sheath 88 is axially displaceable along the axis X-X' around the stent 80 between a distal position shown in FIG. 1 which it adopts in the configuration for insertion, an intermediate position shown in FIG. 2 and a proximal withdrawal position (not illustrated) which it adopts in the configuration for release of the implant 20.

Figure 3:
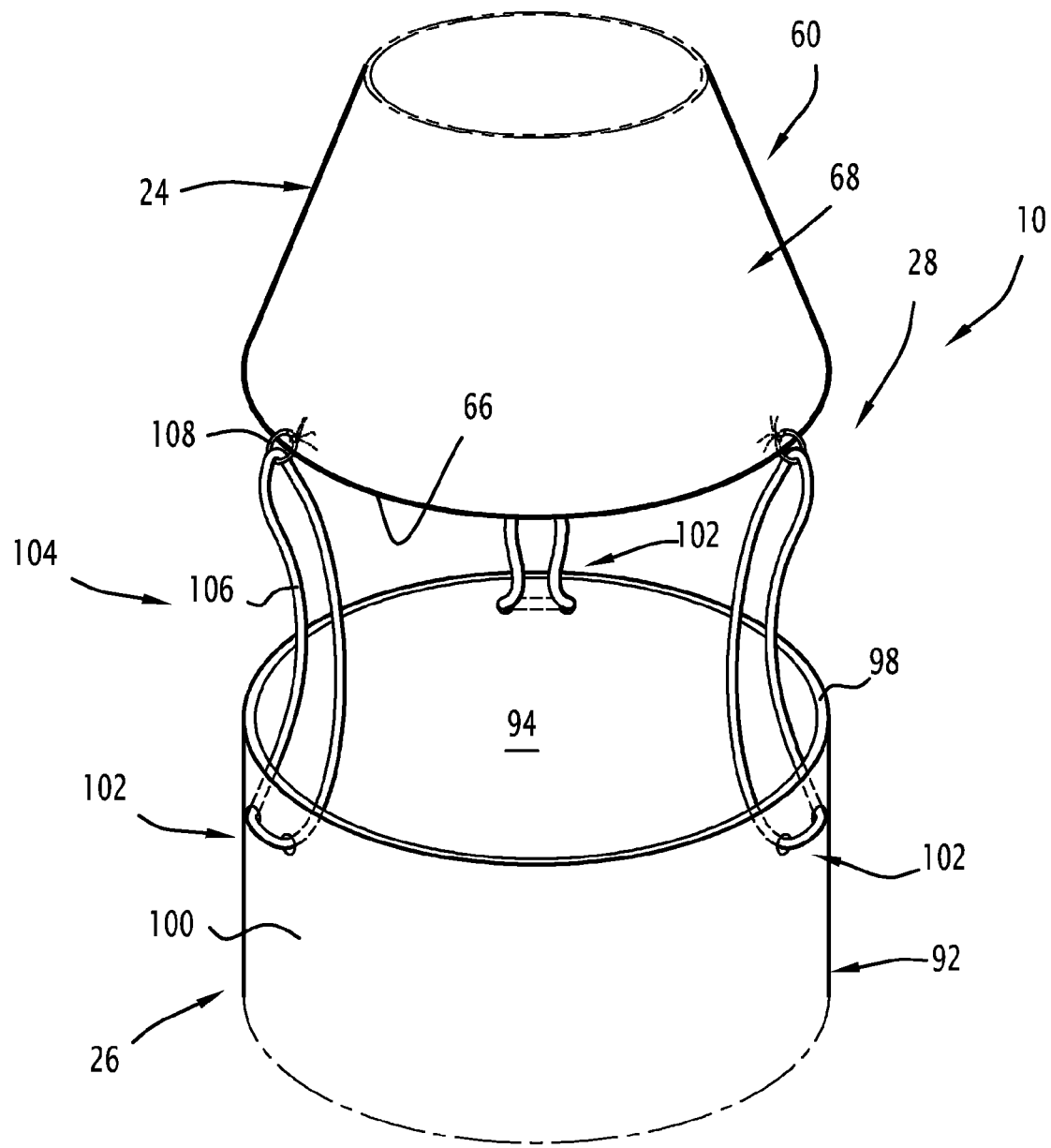
FIG. 3 is a view, in part perspective, of the actuation ties of the implant in the treatment device of FIGS. 1 and 2.

With reference to FIG. 3, the head 92 comprises a cylindrical wall 100 which, in the vicinity of the distal edge 98, defines three pairs of eyelets 102 spaced angularly about the axis X-X'.

The eyelets 102 are arranged through the wall 100 to open into the housing 94 and on the outside of the wall 100 not facing the housing 94.

In the distal position which can be seen in FIG. 1, the distal edge 98 of the sheath 84 is laid flat against the tip 88. The cylindrical wall 100 extends facing the implant 20. The housing 94 is closed at the top by the tip 88.

In the intermediate position, which can be seen in FIG. 2, the sheath 84 has been partly displaced towards the proximal end of the stent 80 to uncover a part of the implant 20 by moving away from the tip 88. The distal edge 98 is then positioned facing the proximal part of the endoprosthesis 30.

In the proximal position, the implant 20 is entirely uncovered and the sheath 84 has been withdrawn outside the patient.

In the first device 10 according to the invention, the means 28 for displacing the interposition member 24 comprise threadlike breakable traction ties 104.

The ties 104 are engaged, on the one hand, in the eyelets 102 situated along the distal edge of the sheath 84 and on the other hand, in the skirt 60, along its free edge 66.

As shown in FIG. 4, each threadlike tie 104 comprises a closed loop of thread 106 and a breakable ring 108.

Each loop 106 is engaged through both eyelets of a pair 102. It therefore has a part projecting into the housing 94 and a part which projects outside said housing, engaged in the ring 108.

The ring 108 is engaged through the fabric forming the skirt 60 along the free edge 66. The thread forming the ring 108 has a much lower tensile strength than that of the thread forming the loop 106. The ring 108 is sewn or knotted in the skirt 60, so that once broken the portions of thread forming it remain integral with the skirt 60.

The functioning of the treatment device 10 according to the invention when introducing an implant 20 into a native valve 12 will now be described.

Initially, the implant 20 is mounted in the deployment tool 26. It is therefore engaged coaxially on the stent 80. The threadlike ties 82 are engaged around the endovalve 22 and are actuated to cause the framework 36 to move from its dilated state of large diameter to its contracted state of low diameter against the stent 80.

Moreover, during mounting, the skirt 60 is placed in its configuration of reduced radial dimension away from the outer surface 40 of the endoprosthesis 30. The free part 68 of the skirt 60 and the cushion 62 therefore extend around the stent 80 between the distal edge 44 and the tip 88. They are laid flat radially towards the axis X-X' against the stent 80.

The sheath 84 is then brought to its distal position by coaxial displacement along the stent 80. The loops 106 are engaged in the eyelets 102 of the sheath 84 and the rings 108 are engaged in the fabric forming the skirt 60.

The deployment tool 26 then adopts its configuration for insertion in the conduit 14, shown in FIG. 1, in which it has the minimum radial dimension, because the interposition member 24 is moved away from the outer surface 40 of the endoprosthesis 30.

Next, the tool 26 is inserted endoluminally in the blood circulation conduit 14. The stent 80 carrying the implant 20 and the sheath 84 are displaced towards the valve 12, until the sheath 84 is interposed between the laminas 18 of the native valve 12 by moving them aside radially.

The stent 80 is held axially fixed and the sheath 84 is partly withdrawn to its intermediate position to partly uncover the implant 20. It is therefore pulled proximally relative to the stent, so that the distal edge 98 is moved away from the tip 88.

During this displacement, and as can be seen in FIG. 2, the threadlike ties 104 tighten. Once the ties 104 are taut, the proximal displacement of the sheath 84 causes traction of the free edge 66 of the skirt 60 towards the proximal edge 42 of the endoprosthesis.

The cushion 62 and the skirt 60 are then turned down around the outer surface 40 of the endoprosthesis 30, until the skirt 60 adopts its turned down configuration.

In this configuration, the skirt 60 and the annular sealing cushion 62 cover the distal part of the endoprosthesis 30 and extend facing the laminas 18 of the native valve.

Next, the surgeon applies strong proximal traction on the sheath 84 to break the breakable rings 108. The sheath 84 is then completely withdrawn outside the patient's body. The surgeon then loosens the threadlike ties 82 to radially expand the framework 36.

During this deployment, the framework 36 moves to its dilated state, and the tool 26 then adopts a configuration for release. The outer surface 40 situated beneath the skirt 60 is applied against the wall 16 delimiting the conduit 14 in the proximal part of the endoprosthesis 30.

In the distal part of the endoprosthesis covered by the skirt 60, the interposition member 24 is positioned between the outer surface 40 and the wall 16 of the conduit 14, or between the surface 40 and the laminas 18. The cushions 62 then occupy the free spaces between the laminas 18, which closes and seals the conduit 14 around the endoprosthesis 30.

During diastole, the blood, which has a tendency to flow back up the conduit 14 from bottom to top in FIG. 4, closes the laminas 48. In addition, the blood cannot pass round the endoprosthesis 30 given the presence of the skirt 60 which opens towards the proximal edge 42 of the endoprosthesis 30 and of the cushions 32.

The risk of leakage through the endovalve 22 and around said endovalve is therefore substantially reduced during diastole.

The ties 82 and the stent 80 are then withdrawn outside the patient's body.

The treatment device 10 according to the invention thus enables an endovalve 22 to be applied in a sealed manner against the outer wall 16 of a blood circulation conduit 14, while having a minimum radial dimension during its insertion in the conduit 14.

In a variant, the surgeon completely uncovers the implant 20, as described above, which causes the skirt 60 to be completely turned down without breaking the ties 104.

Next, he loosens the threadlike ties 82 to radially expand the endoprosthesis. Having done this, and if the positioning is satisfactory, he then applies strong proximal traction to break the ties 104 and release the sheath 84.

Figure 6:
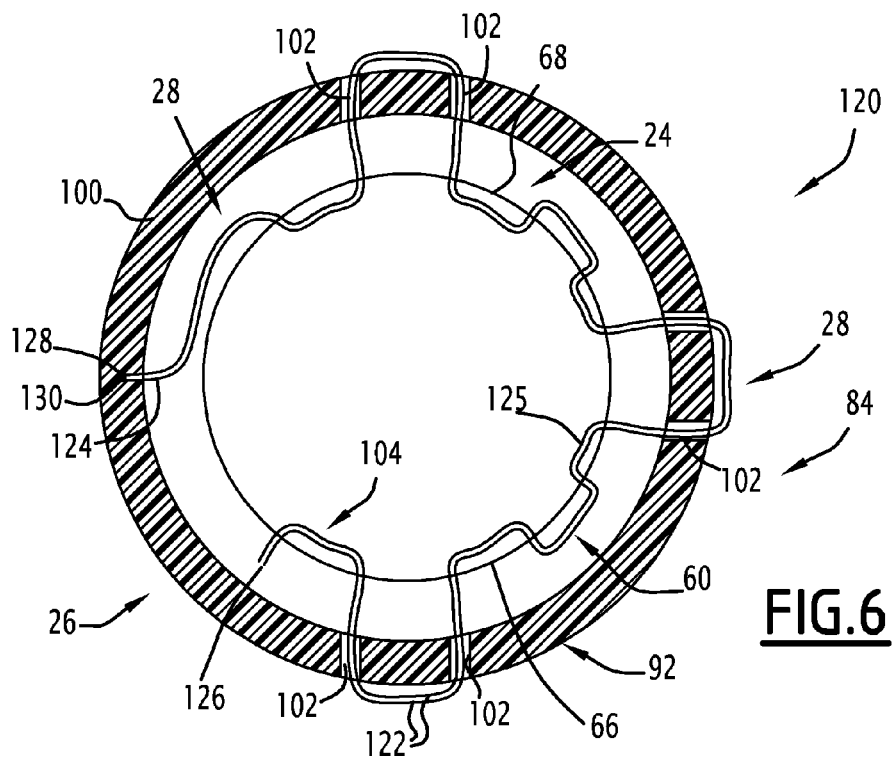
FIG. 6 is a diagrammatic view in part cross-section along the transverse plane VI-VI of FIG. 5.
Figure 5:
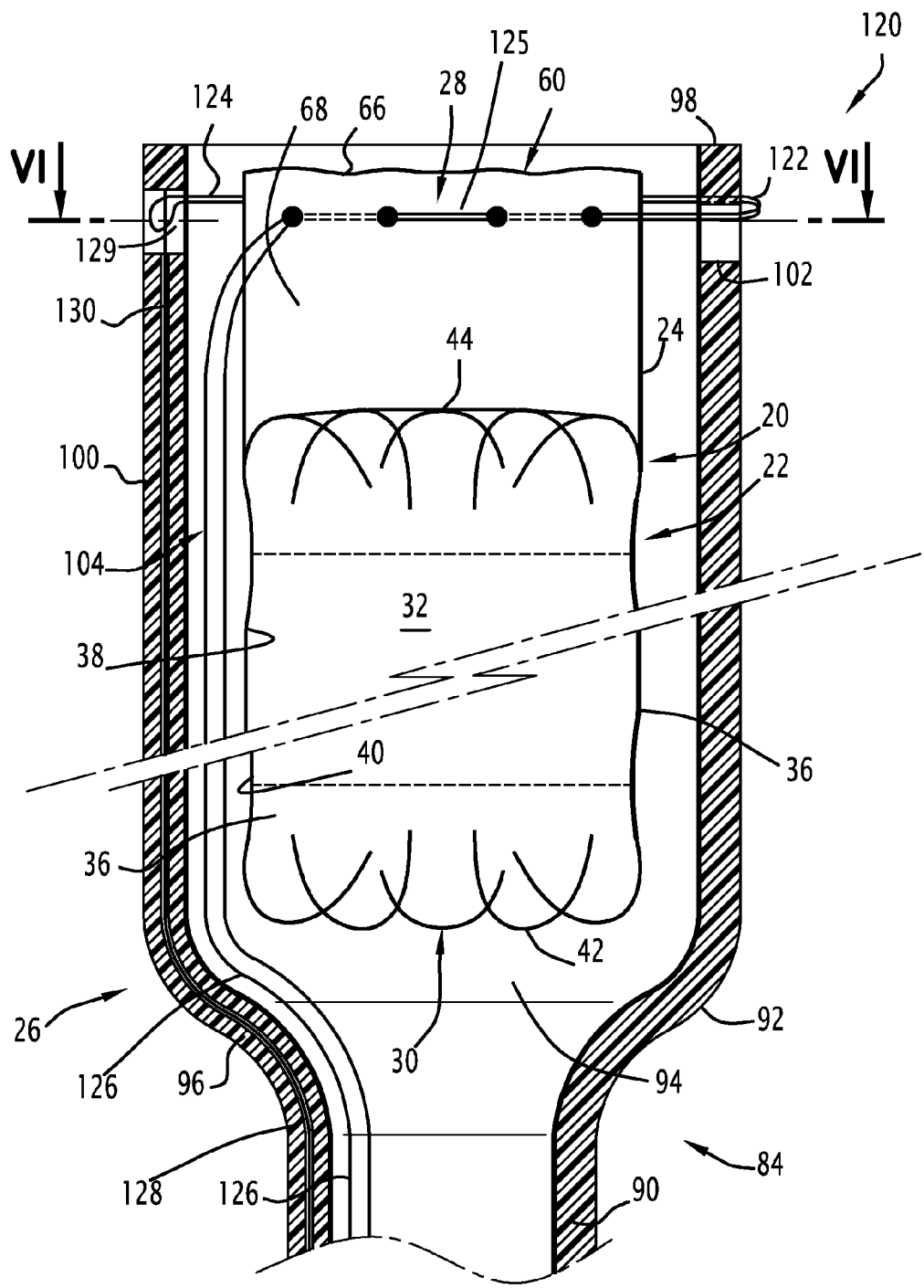
FIG. 5 is a view in part cross-section along an axial midplane of the relevant parts of a second treatment device according to the invention.

The second device 120 according to the invention, shown in FIGS. 5 and 6, differs from the first device 10 in the nature of the displacement means 28.

In the second device 120, the displacement means 28 comprise a single threadlike tie 104 made up of two strands of thread 122 folded in a loop 124 at their distal end. The strands of thread 122 have a distal retention portion 125 engaged successively and alternately through the eyelets 102 and through the skirt 60 along its free edge 66. The threads 122 also form a proximal control portion 126 which extends longitudinally through the sheath 84 to the proximal end of the stent 80 so that a surgeon can actuate it by traction outside the patient.

Moreover, the cylindrical wall 100 defines internally an axial circulation passage 128 which opens out radially towards the axis X-X' in the housing 94 through a radial retention opening 129.

The displacement means 28 comprise a pin 130 for retaining the loop 124 inserted in the passage 128 which extends to the proximal end of the stent 80 to be actuated by the surgeon. The pin 130 is displaceable between a distal retention position in which it holds the loop 124 facing the radial opening 129, and a proximal withdrawal position in which it has been extracted from the loop 124 away from the retention opening 129.

Initially and when the skirt 60 is displaced in order to turn it down around the outer surface 40 of the endoprosthesis 30, the pin 130 occupies its distal position engaged in the loop 124. The strands of thread 122 engaged in the skirt 60 are then held axially relative to the sheath 84 by the eyelets 102. The proximal displacement of the sheath 84 thus causes a proximal displacement of the free edge 66 of the skirt 60.

When the skirt 60 has been completely turned down, the pin 130 is pulled towards its proximal position to release the loop 124. The surgeon then pulls the control portion 126, which extracts the retention portion 125 and the loop 124 outside the skirt 60 and the eyelets 102 to bring them outside the human body. The sheath 84 is then completely released from the implant 20.

Figure 7:
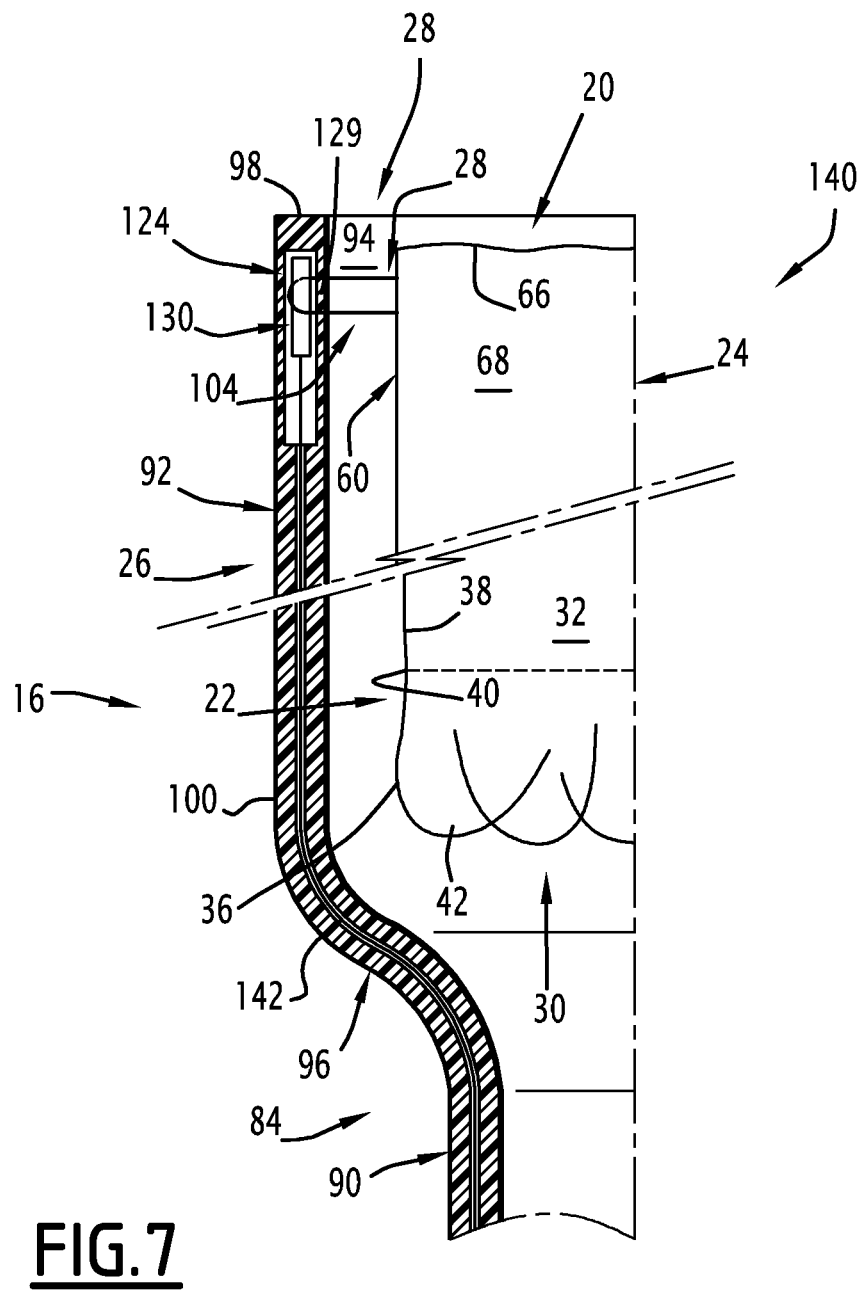
FIG. 7 is a view similar to FIG. 5 of a detail of a third treatment device according to the invention.

In the variant shown in FIG. 7, the pin 130 only extends into a housing shorter in length than the wall 100 and arranged in the wall 100. It is extended at its proximal end by a control thread 142 which is more flexible than the pin 130 which extends to the proximal end of the stent 80.

The thickness of the thread 142 is very much less than that of the pin 130. The thread 142 can be actuated by the surgeon to release the tie 104 from the pin 130, as described above.

Figure 8:
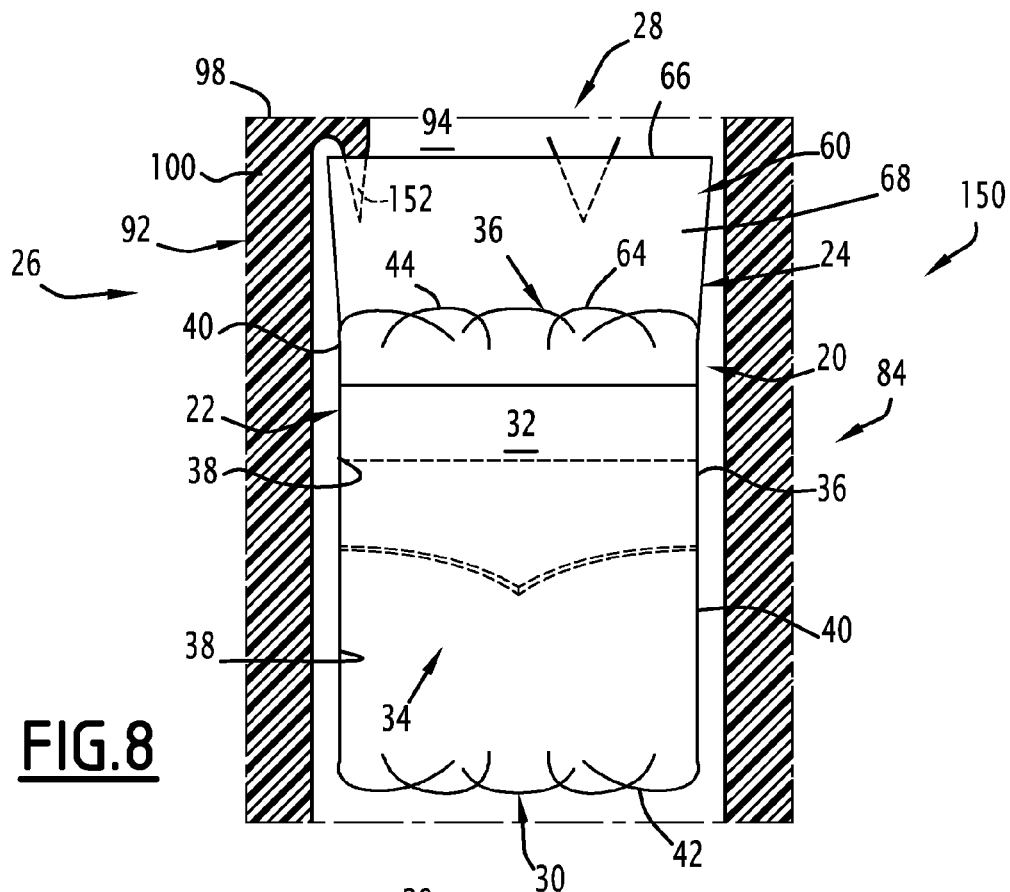
FIG. 8 is a view similar to FIG. 5 of a fourth treatment device according to the invention.

The fourth device 150 according to the invention, shown in FIG. 8, differs from the first device 10 in that the displacement means 28 consist of hooks 152 which are integral with the cylindrical wall 100. The hooks 152 project downwards in the housing 94 from the wall 100. They are made for example in a single piece with the wall 100.

The free edge 66 of the skirt 60 is interposed between the wall 100 and each hook 152 when it adopts its configuration of reduced radial dimension.

The turning down of the skirt 60 around the surface 40 is caused by the displacement of the hooks 150 towards the proximal end of the stent 80 during the displacement of the sheath 84 from its distal position to its proximal position.

Figure 9:
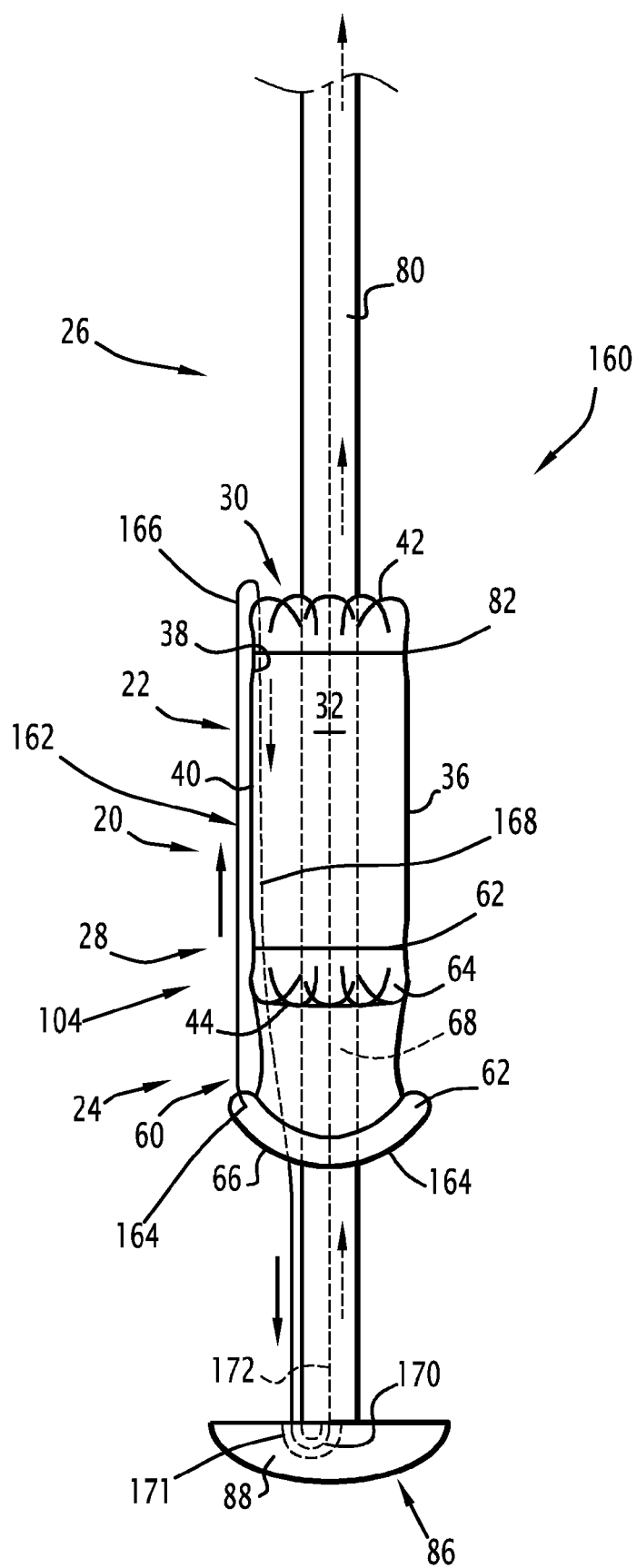
FIG. 9 is a view similar to FIG. 5 of a fifth treatment device according to the invention.

The fifth device 160 according to the invention, shown in FIG. 9, differs from the first device 10 in that the displacement means 28 of the skirt are independent of the sheath 84. The displacement means 28 comprise a plurality of displacement threads 162, spaced angularly about the axis X-X', only one of which is shown in FIG. 9.

Each thread 162 extends between a distal end 164 fixed releasably to the free edge 66 of the skirt 60, and a proximal end (not illustrated) which projects outside the stent 80, at the proximal end thereof.

Each thread 162 has, from the distal end 164, a first axial portion 166 extending outside and along the skirt 60 and the outer surface 40 to the proximal edge 42 of the framework 36, then a second portion 168 which extends in the passage 28 and inside the skirt 60 to the tip 88.

Each thread 164 then has a third portion 170 engaged in an elbowed retention passage 170, arranged in the tip 88, and a fourth portion 172 which extends through the stent 80 to the proximal end of the stent 80.

When the surgeon pulls on the proximal end of the thread 162, it causes the distal end 164 to be displaced towards the proximal edge 42 of the endoprosthesis 30. This reduces the length of the first portion 166 and the length of the second portion 168, which brings the distal end 164 closer to the proximal edge 42. The skirt 60 is turned down around the endoprosthesis 30.

Figure 10:
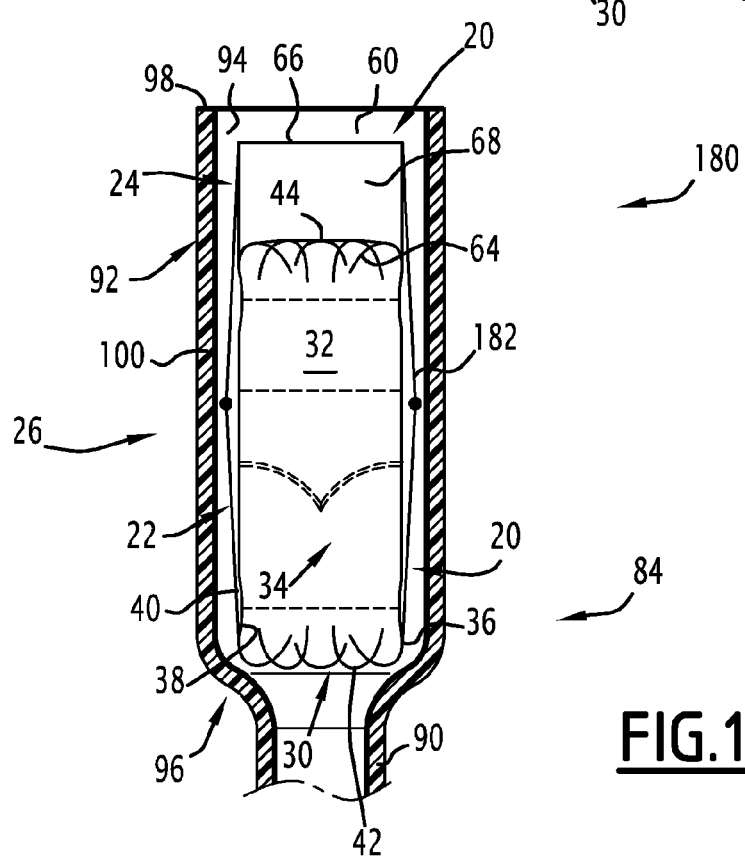
FIG. 10 is a view similar to FIG. 5 of a sixth treatment device according to the invention.

The sixth device 180 according to the invention, shown in FIG. 10, differs from the first device 10 in that the interposition member 24 is spontaneously displaceable from a configuration of reduced dimension to its turned-down configuration.

The interposition member 24 therefore comprises a plurality of resilient fasteners 182 which are axially extendable between an unstable position of maximum extension length and a folded position of minimum length, which constitutes their rest position. Each of the fasteners 182 is connected, on the one hand, to the outer surface 40 of the endoprosthesis 30 and, on the other hand, to the free edge 66 of the skirt 60.

When the implant 20 is loaded in the deployment tool 26, the fasteners 182 are placed in their unstable extension position and held in this position by the sheath 84. The skirt 60 then adopts its configuration of reduced radial dimension.

When the sheath 84 is withdrawn to uncover the implant 20, the fasteners 182 move spontaneously into their folded position, which causes the skirt 60 to be turned down around the outer surface 40.

Figure 11:
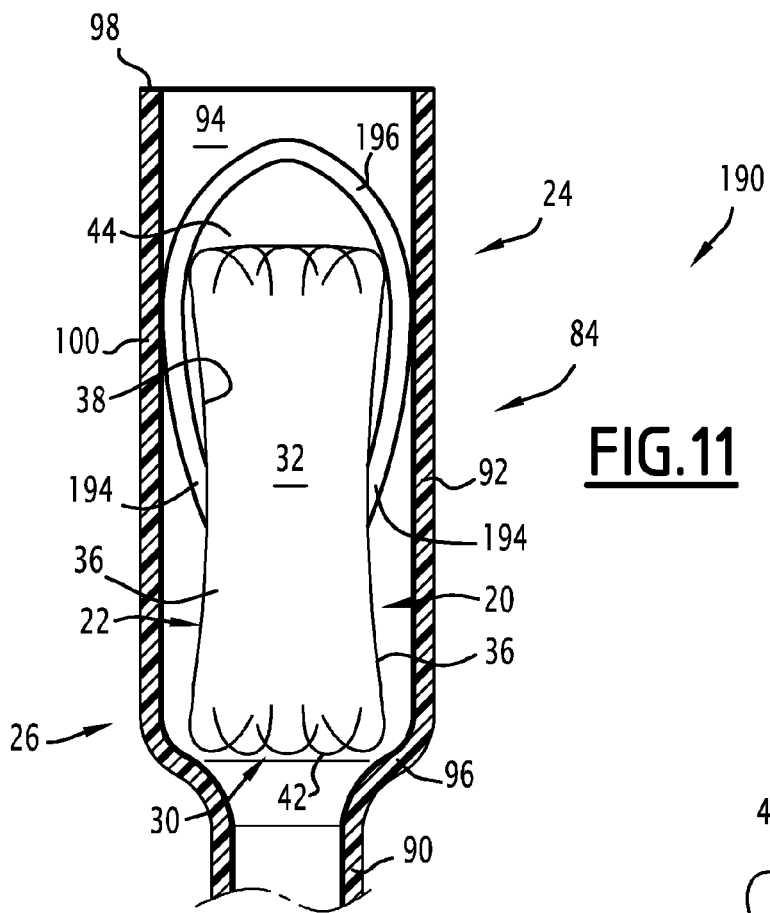
FIG. 11 is a view similar to FIG. 5 of a seventh treatment device according to the invention.
Figure 12:
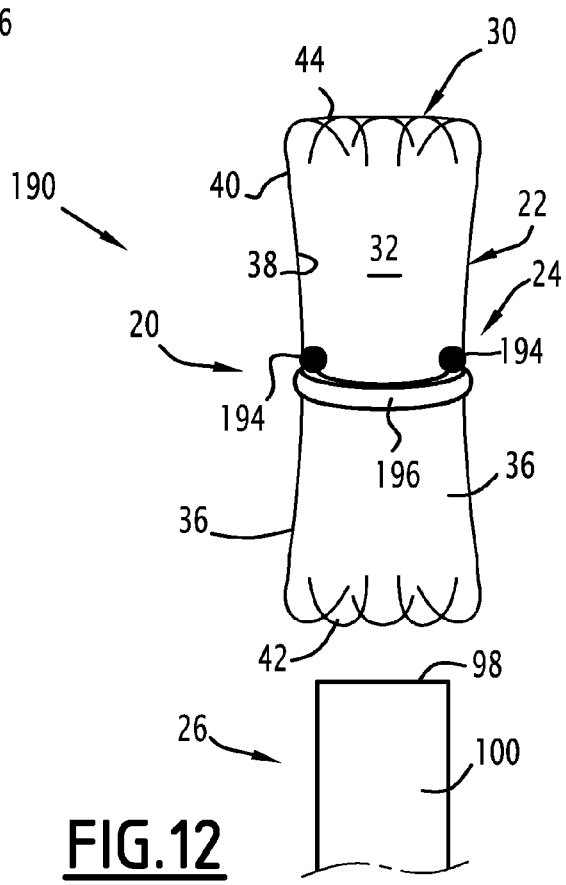
FIG. 12 is a view similar to FIG. 4 of the seventh treatment device.

The seventh treatment device 190 according to the invention, shown in FIGS. 11 and 12, differs from the first device 10 in that it comprises a plurality of interposition members 24 distributed angularly about the axis X-X' along a circumference of the outer surface 40. Each interposition member 24 lacks a skirt and comprises a roll 192 made of deformable foam.

Each roll 192 is fixed to the outer surface 40 at its ends at two points 194 spaced angularly about the axis X-X'. Each roll 192 defines, between its fixing points 194, a portion 196 which is freely displaceable relative to the outer surface 40. This portion 196 is deformable between an unstable configuration of minimum radial dimension shown in FIG. 11, and a configuration for interposition shown in FIG. 12, which constitutes its rest configuration.

In the configuration of minimum radial dimension, part of the portion 196 has been axially displaced away from the outer surface 40 beyond the distal edge 44. This part is held beyond the surface by the sheath 84.

When the sheath 84 is withdrawn, the part 196 is spontaneously displaced by deformation to its configuration for interposition. In this configuration, it is laid flat against the surface 40 along a circumference, between its fixing points 194.

Figure 13:
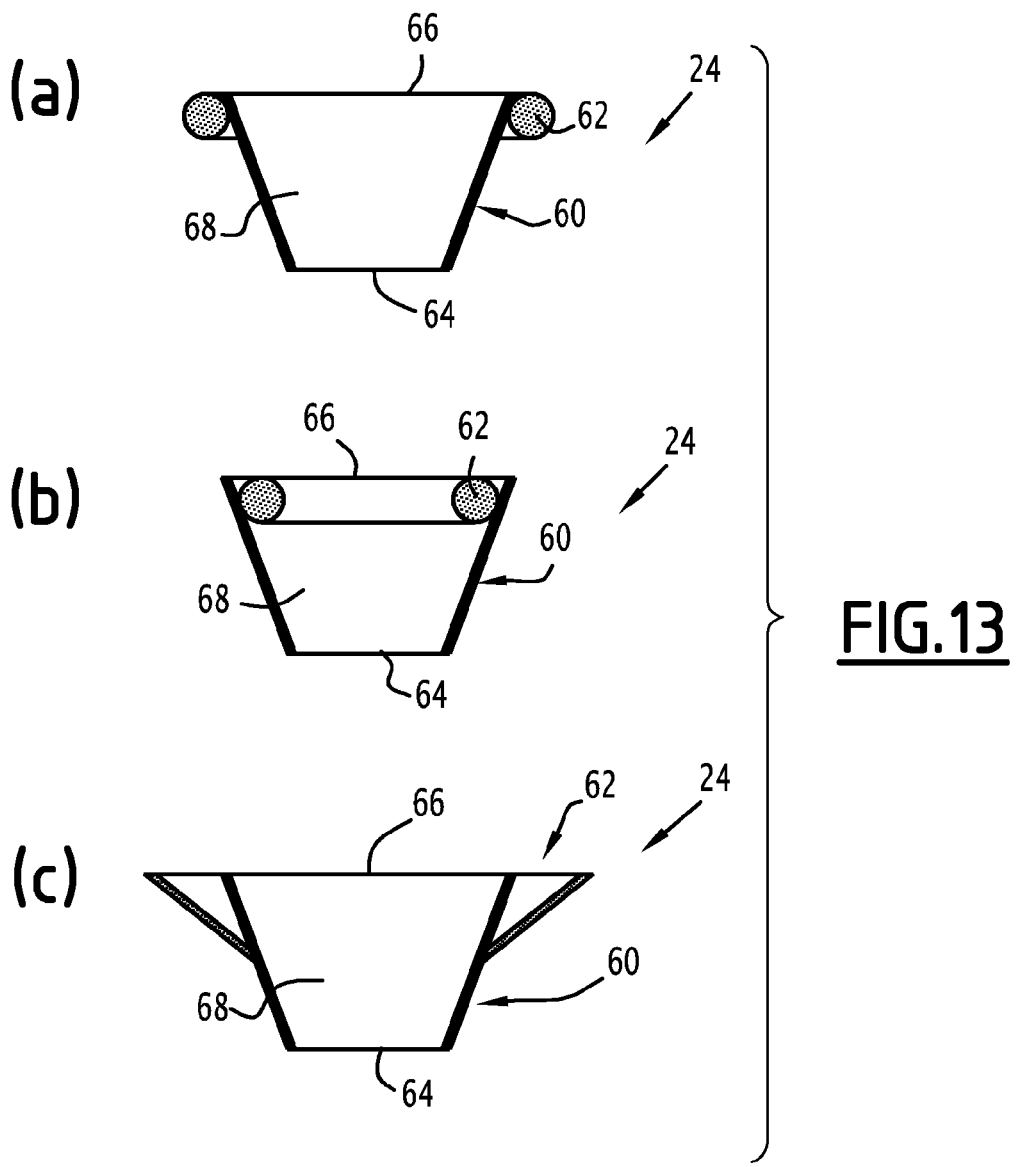
FIG. 13 is a view illustrating variants of implant interposition members for a treatment device according to the invention.

Variants of interposition members 24 are shown in FIG. 13. In the variant (a), the interposition member 24 comprises a peripheral skirt 60 and an annular cushion 62 formed by a deformable roll attached to the outer surface of the skirt 60, when the skirt 60 is in its configuration of minimum radial dimension. In the variant (b), the cushion 62 is attached to the inner surface of the skirt 60 when the skirt 60 is in its configuration of minimum radial dimension.

In the variant (c), the annular cushion 62 is formed by a fold of fabric.

Figure 15:
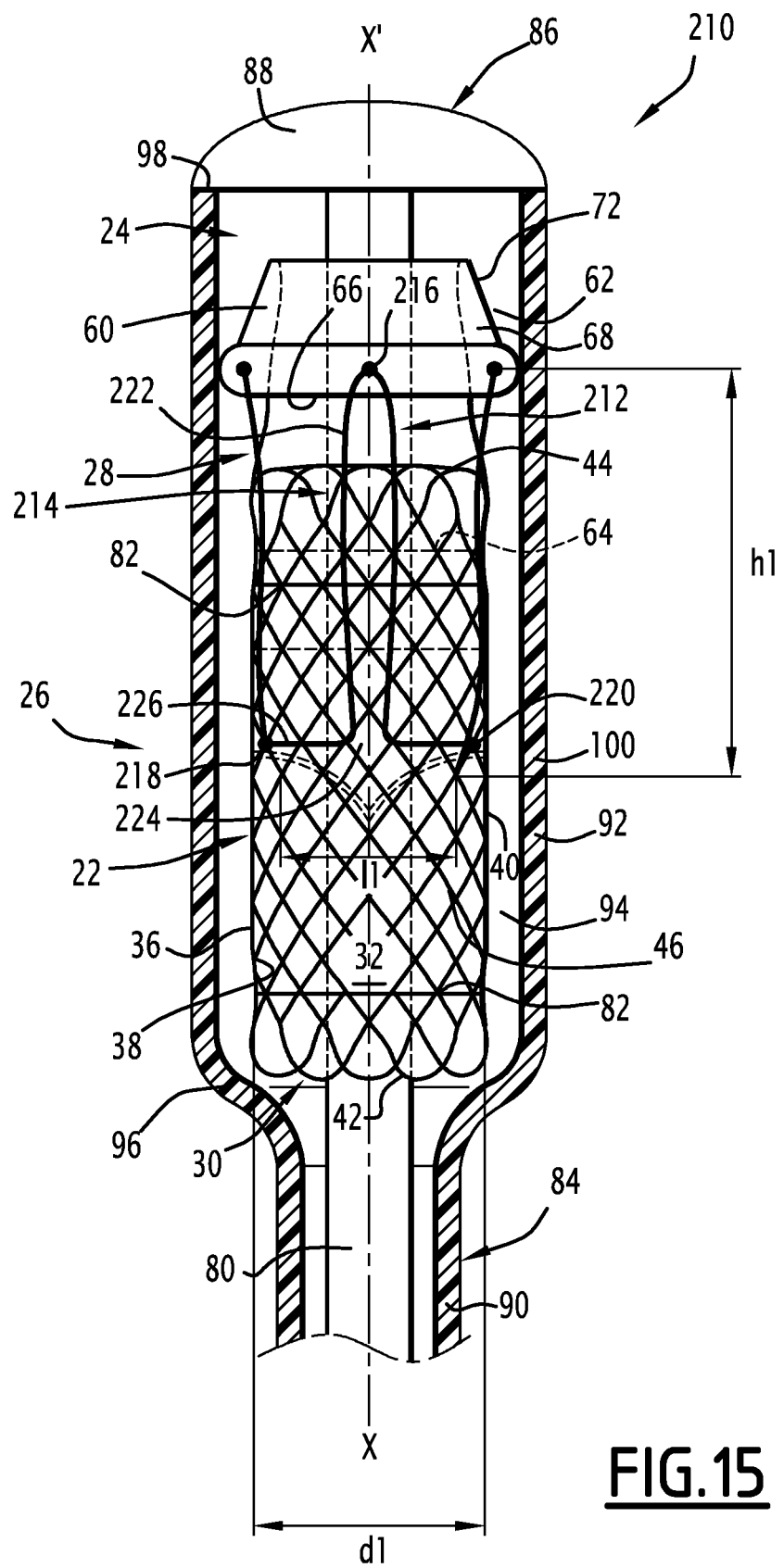
FIG. 15 is a view similar to FIG. 1 of an eighth treatment device according to the invention.
Figure 16:
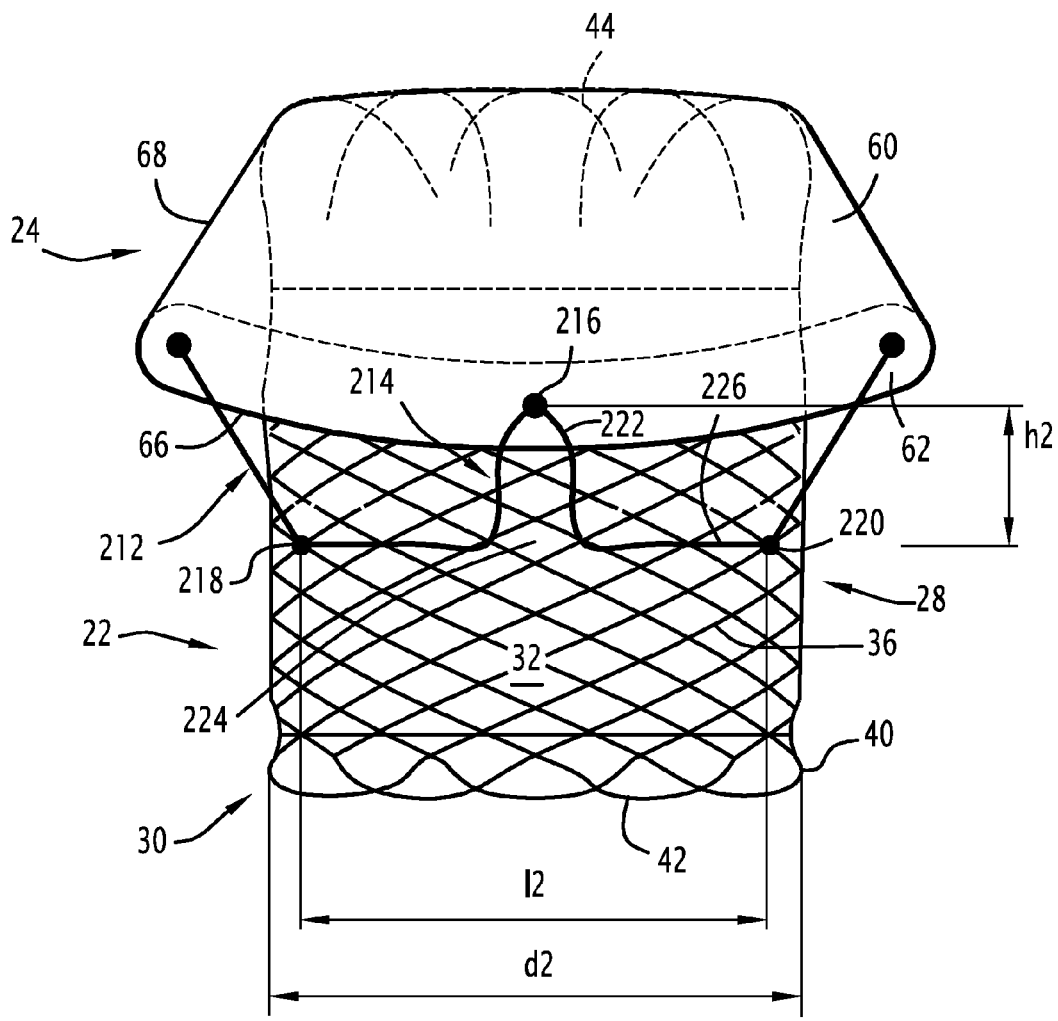
FIG. 16 is a view similar to FIG. 2 of the eighth treatment device according to the invention after withdrawal of the deployment tool.

An eighth treatment device 210 according to the invention is shown in FIGS. 15 and 16. Unlike the first device 10, the eighth device 210 comprises a non-breakable threadlike tie 212 for actuating the interposition member 24, connecting the free edge 66 of the interposition member 24 to the framework 36.

The threadlike tie 212 therefore comprises at least one actuation portion 214 in the form of a boss. The portion 214 has a first connection point 216 fixed to the interposition member 24 and second and third connection points 218, 220 fixed to the framework 36.

The first connection point 216 is fixed for example in the vicinity of the free edge 66 of the skirt 60 as described above. It is placed angularly about the axis X-X' between the second connection point 218 and the third connection point 220.

The second connection point 218 and the third connection point 220 are situated substantially in the same plane P perpendicular to the axis X-X', being spaced angularly about the axis X-X'.

The second connection point 218 and the third connection point 220 are fixed for example to the threads forming the mesh of the framework 36.

The actuation portion 214 has, between the first connection point 216 and each of the second 218 and the third 220 connection points, an axial section 222 extending substantially along a generatrix of the framework 36 to a link 224 situated substantially in the plane P, and a circumferential section 226 engaged through the link 224 and extending along the framework 36 to the second connection point 218 and the third connection point 220 respectively.

The threadlike tie 212 is substantially non-extendable and its length therefore remains substantially constant.

When the deployment tool 26 is in its configuration for insertion, the framework 36 is in its contracted state shown in FIG. 15.

The length h1 of the axial section 222 of the portion 214, taken along the axis X-X' between the first connection point 216 and the link 224 is maximal and is greater than the distance which separates the link 224 from the distal edge 44 of the endoprosthesis 30. The first connection point 216 then occupies a position axially remote from the first and second connection points 218, 220.

The skirt 60 and the annular cushion 62 are then in their configuration of minimum radial dimension in the axial extension of the endoprosthesis 30. The first connection point 216 is also situated beyond the distal edge 44 axially away from the endoprosthesis 30.

In addition, the distance l1 which separates the second connection point 218 from the third connection point 220 is minimal, as is the diameter d1 of the framework 36 of the endoprosthesis 30.

When the deployment tool 26 moves from its configuration for insertion of the implant 20 in the conduit 14 to its configuration for release of the implant 20, the framework 36 of the endoprosthesis 30 is deployed from its contracted state to its dilated state during the loosening of the threadlike ties 82.

As shown in FIG. 16, the diameter d2 of the framework 36 increases. The second connection point 218 then moves away from the third connection point 220 and the distance l2 which separates these two points in the dilated state of the framework 36 is greater than the distance l1 which separates these two points in the contracted state.

This increase in distance causes an increase in the length of the circumferential sections 226 of the actuation portion 214 and the corresponding reduction in the length of the axial sections 222.

The first connection point 216 thus moves closer axially to the link 224 and the plane P perpendicular to the axis X-X' containing the second connection point 218 and the third connection point 220 until the first point 216 occupies a position axially closer to the second point 218 and to the third point 220, in which it is positioned facing the outer surface 40 of the framework 36.

The length h2 of the axial sections 222, taken between the first point 216 and the link 224 is thus minimal.

The displacement of the first connection point 216 fixed to the free edge 66 of the skirt 60 causes the skirt 60 to be turned down against the outer surface 40 of the framework 36 to its configuration for interposition between the endoprosthesis 30 and the conduit 14.

Generally, the tie 212 may consist of a single and continuous strand of thread comprising several similar actuation portions 214 distributed around the periphery of the framework 36.

In a variant, the tie 212 is engaged in the skirt 60 at a connection point 216 in the region of the free edge 66 without being fixed to the skirt 60. Similarly, the tie 212 is engaged in two respective links of the framework 36 spaced angularly about the axis X-X' without being fixed to the framework 36 in the region of the second and third connection points 220, 222 with the framework 36.

As shown in FIG. 1, the valve 34 and the interposition member 24 are separate and independent of one another.

Thus, the connection edge 64 is situated axially away from the valve 34.

Moreover, as shown in FIG. 16, the maximum circumference of the free edge 66 of the interposition member is greater than the maximum circumference of the distal edge of the framework 36 in its dilated state.

Figure 17:
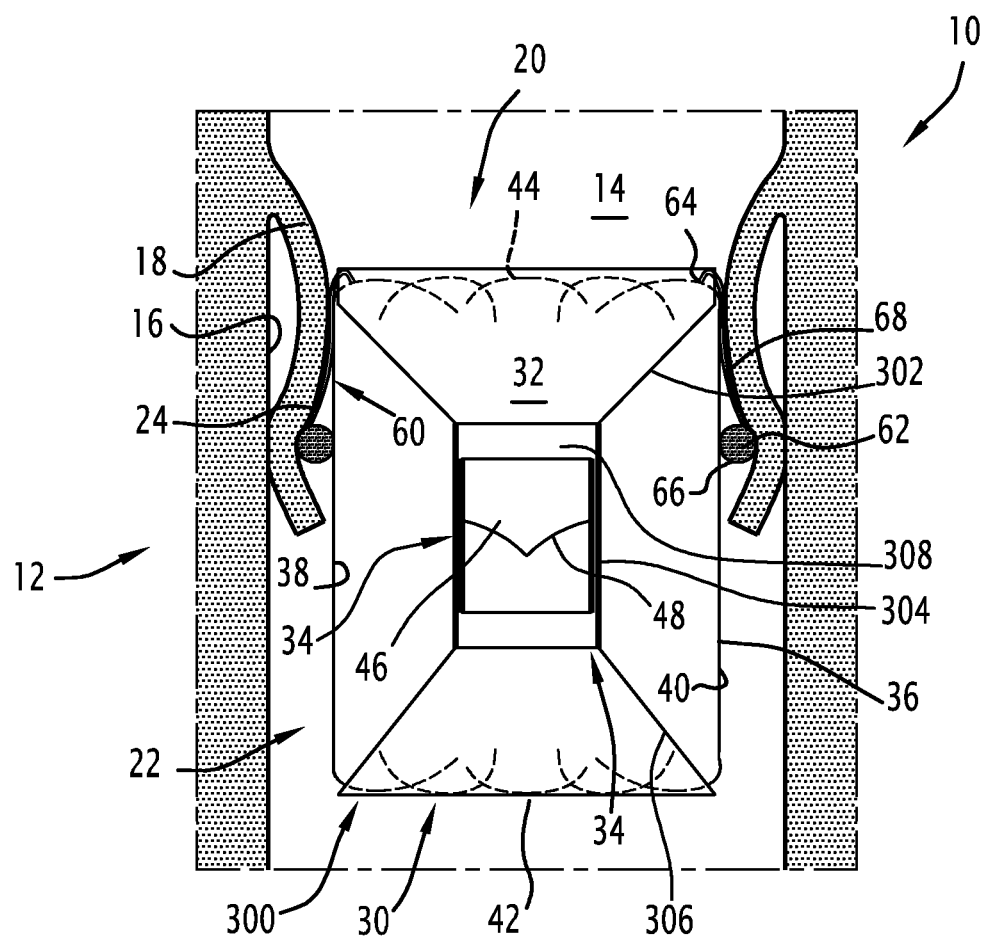
FIG. 17 is a view similar to FIG. 4 of a ninth treatment device according to the invention.

In a variant illustrated diagrammatically in FIG. 17, the endovalve 22 comprises internally a valve reducer 300 which is more flexible than the framework 36 so that it can be folded in the central passage 32 when the framework 30 occupies its contracted state and can be deployed in the central passage 32 when the framework 36 is in its dilated state. A reducer of this type is described in application FR 07 55355 of the applicant.

This valve reducer 300 comprises a sealed distal skirt 302 of convergent cross-section towards the proximal edge 42, a tubular inner wall 304 shorter in length than the framework 36 and smaller in diameter than the framework 36, and a proximal skirt 306 of convergent cross-section towards the distal edge 44.

The proximal skirt 306, the tubular inner wall 304 and the distal skirt 302 are produced advantageously in a single piece and made of a deformable material, for example a fabric such as Dacron® or a plastic film.

The distal skirt 302 is fixed to the framework 36 along the distal edge 44. It extends converging towards the proximal edge 42 as far as a distal edge of the inner wall 304.

The proximal skirt 306 is fixed along the proximal edge 42. It extends converging towards the distal edge 44 as far as a proximal edge of the inner wall 304.

The inner wall 304 thus defines a hole 308 of smaller diameter than the central passage 32.

The valve 34 is advantageously fixed permanently or movably in the hole 308 delimited internally by the wall 304.

As described in detail in FR 07 55355, the skirts 302, 306 and the wall 304 are covered internally by a sealed coating so that they guide the blood through the hole 308 and the valve 34, preventing the blood from passing into the spaced delimited annularly between the skirts 302, 306 and the framework 36.

The invention claimed is:

1. A device for treating a blood circulation conduit (14), comprising:
   an implant (20) for placing in the conduit (14), the implant (20) that comprising
   a tubular endoprosthesis (30) with an axis (X-X') having a framework (36) which is radially deployable between a contracted state and a dilated state, the framework (36) having an outer surface (40) delimited axially by an axial edge (44), and
   at least one interposition member (24) which is more flexible than the framework (36), the interposition member (24) being mounted movably on the endoprosthesis (30) for interposition between the outer surface (40) and the conduit (14); and a deployment tool (26) for deploying the implant (20), the deployment tool (26) being configured to adopt a configuration for insertion of the implant (20) in the conduit (14), in which the deployment tool (26) holds the framework (36) in the contracted state, and a configuration for release of the implant (20), in which the framework (36) adopts the dilated state, wherein, in the configuration for insertion, the interposition member (24) comprises at least one free part (68) that is held axially away from the outer surface (40) beyond the axial edge (44) to minimise the radial dimension of the implant (20), the free part (68) being at least partly displaceable against the outer surface (40) when the deployment tool (26) moves from the configuration for insertion to the configuration for release, wherein the interposition member (24) comprises a flexible peripheral skirt (60) having a connection edge (64) fixed to the endoprosthesis (30) and a free edge (66), the skirt (60) being displaceable between a configuration of reduced radial dimension in which the free edge (66) is placed axially away from the axial edge of the outer surface, which the skirt (60) adopts in the configuration for insertion, and a turned-down configuration that is turned down against the outer surface, which the skirt (60) adopts in the configuration for release, and wherein the interposition member further comprises at least one radial sealing cushion (62) which projects radially relative to the skirt (60) and is attached to an outside of the skirt (60) along the free edge (66) of the skirt (60).

2. The device according to claim 1, further comprising:
at least one actuation tie (104) for actuating the interposition member (24), the at least one actuation tie (104) releasably connecting the free part (68) and the deployment tool (26),
the at least one actuation tie (104) being axially displaceable relative to the endoprosthesis (30) to pull the free part (68) towards the outer surface (40) when the deployment tool (26) moves from the configuration for insertion to the configuration for release.

3. The device according to claim 2, wherein the at least one actuation tie (104) is breakable by axial traction.

4. The device according to claim 3, wherein the deployment tool (26) comprises a sheath (84) for housing the implant (20), which is axially displaceable relative to the implant (20), the at least one actuation tie (104) being engaged releasably in the sheath (84), a displacement of the sheath (84) away from the endoprosthesis (30) causing a displacement of the free part (68) towards the outer surface (40) by traction on the tie (104).

5. The device according to claim 2,
wherein the at least one actuation tie (104) comprises a locking loop (124), and
wherein the deployment tool (26) comprises a pin (130), the pin (130) being movable between an engaged position in the locking loop (124), in which an axial displacement of the at least one actuation tie (104) relative to the endoprosthesis (30) causes an axial displacement of the free part (68) relative to the endoprosthesis (30), and a released position outside the locking loop (124), in which the axial displacement of the at least one actuation tie (104) causes the at least one actuation tie to be released relative to the free part (68).

6. The device according to claim 5, wherein the deployment tool (26) comprises a sheath (84) for housing the implant (20), which is axially displaceable relative to the implant (20), the at least one actuation tie (104) being engaged releasably in the sheath (84), a displacement of the sheath (84) away from the endoprosthesis (30) causing a displacement of the free part (68) towards the outer surface (40) by traction on the tie (104).

7. The device according to claim 2, wherein the deployment tool (26) comprises a sheath (84) for housing the implant (20), which is axially displaceable relative to the implant (20), the at least one actuation tie (104) being engaged releasably in the sheath (84), a displacement of the sheath (84) away from the endoprosthesis (30) causing a displacement of the free part (68) towards the outer surface (40) by traction on the tie (104).

8. The device according to claim 2, wherein the deployment tool (26) comprises a stent (80) for holding the endoprosthesis (30) axially before the radial deployment of the framework (36), the actuation tie (104) being engaged in the stent (80) and being movable relative to the endoprosthesis (30) through the stent (80) in order to be actuated from a proximal end of the stent (80).

9. The device according to claim 1, wherein the framework (36) has an inner surface (38) delimiting a central blood circulation passage (32), the implant (20) comprising a valve (34) fixed to the inner surface (38) to selectively close the central passage (32).

10. The device according to claim 1, further comprising:
at least one actuation tie (212) for actuating the interposition member, the actuation tie (212) having at least a first connection point (216) to the interposition member (24), and at least second and third connection points (218, 220) to the framework (36), the second and third connection points (218, 220) being spaced angularly on the framework (36) about the axis (X-X'),
wherein the movement of the framework (36) of the endoprosthesis (30) between the contracted state and the dilated state causes a distance separating the second connection point (218) and the third connection point (220) to increase, and causes an axial displacement of the first connection point (216) between a position axially remote from the second and third connection points (218, 220) and a position axially closer to the second and third connection points (218, 220), in which the first connection point (218) is situated facing the outer surface (40).

11. The device according to claim 1, wherein the deployment tool (26) comprises a stent (80) to support and axially maintain an endovalve (22) in the conduit (14), and threadlike ties (82) for holding the framework (36) in the contracted state against the stent (80), the threadlike ties (82) being configured to be actuated between a configuration for holding the framework (36) in the contracted state against the stent (80), and a configuration for release of the framework (36) in which the framework (36) adopts the dilated state, the threadlike ties (82) being configured to be loosened thereby to radially expand the framework (36) after the skirt (60) moves from the configuration of reduced radial dimension to the turned-down configuration.

12. The device according to claim 1, wherein the implant (20) also comprises a valve reducer (300) which is more flexible than the framework (36) arranged in a central blood circulation passage (32), the valve reducer (300) comprising a tubular inner wall (304) carrying a valve (34), of smaller diameter than the central blood circulation passage (32), a distal skirt (302) for connection to the framework (36), and a proximal skirt (306) for connection to the framework (36).

13. The device according to claim 1, wherein the radial sealing cushion (62) is annular.

* * * * *

UNITED STATES PATENT AND TRADEMARK OFFICE
CERTIFICATE OF CORRECTION

PATENT NO.        : 8,512,396 B2  
APPLICATION NO.   : 12/677314  
DATED             : August 20, 2013  
INVENTOR(S)       : Witold Styrc Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 525 days.

Signed and Sealed this

Fifteenth Day of September, 2015

Michelle K. Lee  
*Director of the United States Patent and Trademark Office*